(12) United States Patent
Ko et al.

(10) Patent No.: US 8,884,071 B2
(45) Date of Patent: Nov. 11, 2014

(54) HYDROFORMYLATION METHOD HAVING IMPROVED CATALYST STABILITY IN REACTION

(75) Inventors: Dong-Hyun Ko, Daejeon (KR); Sung-Shik Eom, Daejeon (KR); Moo-Ho Hong, Daejeon (KR); O-Hak Kwon, Daejeon (KR); Jae-Hui Choi, Daejeon (KR); Dae-Chul Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/125,886

(22) PCT Filed: Jun. 4, 2012

(86) PCT No.: PCT/KR2012/004408
§ 371 (c)(1),
(2), (4) Date: Dec. 12, 2013

(87) PCT Pub. No.: WO2013/183796
PCT Pub. Date: Dec. 12, 2013

(65) Prior Publication Data
US 2014/0135533 A1 May 15, 2014

(51) Int. Cl.
| | |
|---|---|
| *C07C 45/50* | (2006.01) |
| *C07C 49/20* | (2006.01) |
| *C07C 47/222* | (2006.01) |
| *C07F 9/6574* | (2006.01) |
| *B01J 31/02* | (2006.01) |
| *C07C 45/56* | (2006.01) |

(52) U.S. Cl.
CPC ............... *C07C 45/56* (2013.01); *C07C 49/20* (2013.01); *C07C 47/222* (2013.01); *C07F 9/65746* (2013.01); *B01J 31/02* (2013.01)
USPC .......................................... 568/451; 568/454

(58) Field of Classification Search
USPC ................................................... 568/451, 454
See application file for complete search history.

(56) References Cited

U.S. PATENT DOCUMENTS

| | | | |
|---|---|---|---|
| 4,668,651 | A | 5/1987 | Billig et al. |
| 4,694,109 | A | 9/1987 | Devon et al. |
| 5,288,918 | A | 2/1994 | Maher et al. |
| 5,364,950 | A | 11/1994 | Babin et al. |
| 5,756,855 | A | 5/1998 | Abatjoglou et al. |
| 6,090,987 | A | 7/2000 | Billig et al. |
| 2002/0177737 | A1 | 11/2002 | Tam et al. |

FOREIGN PATENT DOCUMENTS

KR  10-0198688  3/1999

*Primary Examiner* — Sikarl Witherspoon
(74) *Attorney, Agent, or Firm* — McKenna Long & Aldridge, LLP

(57) ABSTRACT

Disclosed is a hydroformylation method having improved catalyst stability in a reaction. Advantageously, provided is a hydroformylation method in which a specific α,β-unsaturated carbonyl compound is incorporated during a hydroformylation reaction to prevent alkyl phosphite decomposed from a phosphite ligand from acting as a catalyst poison, thereby improving a yield of reaction and inhibiting decomposition of ligand and catalyst.

9 Claims, No Drawings

HYDROFORMYLATION METHOD HAVING IMPROVED CATALYST STABILITY IN REACTION

This application is a 371 National Stage Application of International Application No. PCT/KR2012/004408, filed Jun. 4, 2012, the disclosure of which is incorporated herein by reference.

TECHNICAL FIELD

The present invention relates to a hydroformylation method having improved catalyst stability in a reaction. More specifically, the present invention relates to a hydroformylation method in which a specific α,β-unsaturated carbonyl compound is put into a hydroformylation reaction to prevent alkyl phosphite decomposed from a phosphite ligand from acting as a catalyst poison, thereby to improve a reaction yield and to inhibit decomposition of ligand and catalyst.

BACKGROUND ART

A hydroformylation reaction wherein linear (normal) and branched (iso) aldehydes in which the number of carbon atoms is increased by one are prepared by reacting various olefins with carbon monoxide (CO) and hydrogen (H2), commonly called synthetic gases, in the presence of a homogeneous organometallic catalyst and a ligand was firstly found by Otto Roelen in 1938 in Germany.

Generally, the hydroformylation reaction known as an oxo reaction is an industrially considerably important reaction in the homogeneous catalyst reaction, various aldehydes including about 8.40 million tons of alcohol derivatives are produced and used through an oxo process (SRI report, November 2002, 682. 7000A) in 2001.

Various aldehydes synthesized through the oxo reaction are converted into acid and alcohol as aldehyde derivatives through an oxidation or hydrogenation process. In addition, after condensation reaction of aldol or the like, aldehydes may be oxidized or hydrogenated and then converted into various acids and alcohols containing a long alkyl group. The alcohol hydrogenated from aldehyde, obtained by this oxo reaction, is referred to as an oxo alcohol. The oxo alcohol is industrially widely used for materials for solvents, additives, various plasticizers and synthetic lubricants.

A metal-carbonyl compound catalyst is known to be active as a catalyst of hydroformylation and the industrially used catalyst is generally based on cobalt (Co) and rhodium (Rh). N/I selectivity (ratio of normal to iso aldehyde) of produced aldehyde depends on the kind of catalyst and ligand, and operation conditions.

At present, 70% or more of oxo process throughout the world uses a low pressure oxo process in which an excess phosphine ligand is applied to a rhodium-based catalyst due to high catalyst activity, high N/I selectivity and relatively easy reaction conditions in spite of problems such as high catalyst cost and deterioration in catalyst activity caused by poisoning.

As a central metal of a catalyst for oxo reaction, a transition metal such as cobalt (Co) and rhodium (Rh) as well as iridium (Ir), ruthenium (Ru), osmium (Os), platinum (Pt), palladium (Pd), iron (Fe), and nickel (Ni) may be used. The respective metals exhibit catalyst activity in the order of Rh>>Co>Ir, Ru>Os>Pt>Pd>Fe>Ni.

Co, Rh, Pt and Ru are Group VIII transition metals, which exhibit superior catalystic activity during an oxo reaction. Pt and Ru are applied to only research application and most of oxo processes for commercial application are based on rhodium and cobalt, and representative examples thereof include $HCo(CO)_4$, $HCo(CO)_3PBu_3$ and $HRh(CO)(PR_3)_3$.

Ligands used for oxo processes include phosphine ($PR_3$, in which R represents $C_6H_5$ or $n-C_4H_9$), phosphine oxide and phosphite. Other ligands containing nitrogen include amines, amides, isonitrile and the like.

However, these ligands have considerably lower catalyst activity than that of ligands containing phosphine due to strong coordination of these ligands to metals thereof. In particular, when rhodium is used as a central metal, almost no ligands superior to triphenylphosphine (TPP) in terms of catalyst activity and stability are known.

Eastman Kodak and Union Carbide (incorporated into Dow Chemical) developed bidentate phosphine ligands that exhibit superior catalyst activity and high N/I selectivity (U.S. Pat. Nos. 4,694,109, 4,668,651), and Dow Chemical is known to apply bisphosphite ligands to some oxo processes.

Meanwhile, U.S. Pat. No. 4,668,651 discloses poly phosphite ligands represented by ligands B described in Examples 6 to 9, but these ligands exhibit considerably low N/I selectivity in spite of considerably superior catalyst activity.

An oxo reaction using phosphite as a ligand is disadvantageous in that the phosphite ligand is decomposed into alkyl phosphite, known as a catalyst poison, during the reaction, deteriorating reaction yield and increasing decomposition of ligand and catalyst.

Korean Patent No. 0198688 discloses a method for converting alkyl phosphite, which is produced as a catalyst poison from a phosphite ligand during a reaction, into a relatively inactive adduct by incorporating a weak acid compound, added water or an epoxide compound, or a method for reducing decomposition of the phosphite ligand. This method cannot satisfactorily improve catalyst yield and stability.

DISCLOSURE OF INVENTION

Technical Problem

Therefore, the present invention has been made in view of solving the above problems, and it is one object of the present invention to provide a hydroformylation method in which a specific α,β-unsaturated carbonyl compound is incorporated into a hydroformylation reaction to prevent alkyl phosphite decomposed from a phosphite ligand from acting as a catalyst poison, thereby to improve reaction yield and to inhibit ligand and catalyst decomposition.

All of these objects can be accomplished by the present invention described below.

Solution to Problem

In accordance with one aspect of the present invention, provided is a hydroformylation method for preparing aldehyde by reacting an olefin-based unsaturated compound with carbon monoxide and hydrogen in the presence of a transition metal-phosphite complex catalyst produced from a transition metal catalyst and a phosphite ligand, wherein the reaction is carried out by further incorporating one or more of compounds represented by the following Formulae 1 to 4.

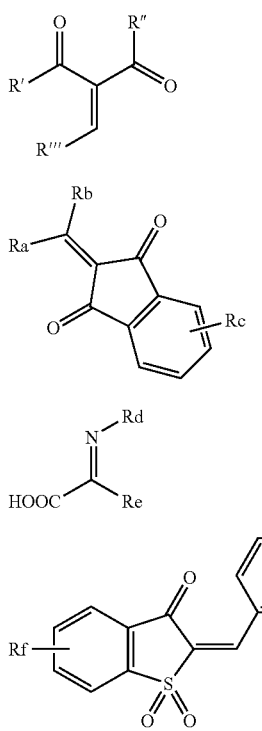

[Formula 1]

[Formula 2]

[Formula 3]

[Formula 4]

Advantageous Effects of Invention

As mentioned above, the present invention has an effect to provide a hydroformylation method in which a specific α,β-unsaturated carbonyl compound is put into a hydroformylation reaction to prevent alkyl phosphite decomposed from a phosphite ligand from acting as a catalyst poison, thereby to improve a reaction yield and to inhibit decomposition of ligand and catalyst.

BEST MODE FOR CARRYING OUT THE INVENTION

Hereinafter, the present invention will be described in detail.

The hydroformylation method having improved catalyst stability during a reaction according to the present invention is a hydroformylation method for preparing aldehyde by reacting an olefin-based unsaturated compound with carbon monoxide and hydrogen in the presence of a transition metal-phosphite complex catalyst produced from a transition metal catalyst and a phosphite ligand, wherein the reaction is carried out by further incorporating one or more of compounds represented by the following Formulae 1 to 4:

[Formula 1]

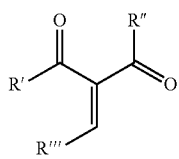

(wherein R' and R" each independently represent a substituted or unsubstituted alkyl group having 1 to 3 carbon atoms, and R'" represents a substituted or unsubstituted aryl group having 6 to 12 carbon atoms),

[Formula 2]

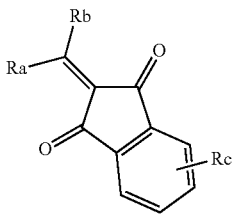

(wherein Ra represents hydrogen, Rb represents a substituted or unsubstituted aryl group having 6 to 12 carbon atoms, and Rc represents hydrogen or an alkyl group)

[Formula 3]

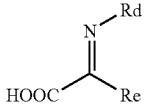

(wherein Rd and Re each independently represent a substituted or unsubstituted aryl group having 6 to 12 carbon atoms)

[Formula 4]

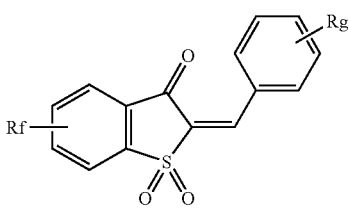

(wherein Rf and Rg each independently represent hydrogen or an alkyl group).

The compounds represented by Formulae 1 to 4 convert alkyl phosphite, a catalyst poison produced by decomposition of a phosphite ligand during the hydroformylation reaction process, into an inactive compound, to maintain the catalyst activity and greatly improve the reaction yield.

Each of the compounds represented by Formulae 1 to 4 is preferably incorporated into 0.5 to 10 moles, more preferably 0.5 to 2 moles, with respect to one mole of a phosphite ligand incorporated during the reaction. Within this range, the catalyst and ligand can be advantageously stabilized.

Although the time and method by which the compounds represented by Formulae 1 to 4 are incorporated are not limited, the compounds are simultaneously incorporated together with a catalyst and phosphite during the reaction process, or the compounds are incorporated when alkyl phosphite, the catalyst poison, is detected, a part of the reacted catalyst is collected and incorporated, and then transferred back to a reactor. Among these methods, one that is easily implemented is preferably used. The former method requires no apparatus for collecting and treating the catalyst, but should simultaneously remove inactive alkyl phosphite continuously precipitated during the process due to treatment with the compounds represented by Formulae 1 to 4. The latter method has effects opposite to the former method.

Each of the compounds represented by Formulae 1 to 4 is preferably maintained in an amount of 0.1 to 5% by weight, more preferably 0.5 to 2% by weight during the hydroformylation reaction. Within this range, the catalyst and ligand can be advantageously stabilized.

The phosphite ligand is preferably a mixture of a bisphosphite ligand and a polyphosphite ligand, or a mixture of a bisphosphite ligand and a monophosphite ligand. In this case, the catalyst activity and N/I selectivity is greatly improved.

The bisphosphite ligand is preferably a compound represented by the following Formula 5.

[Formula 5]

wherein $R_1$ to $R_8$ and $R_1'$ to $R_8'$ are each independently different or identical, and represent hydrogen, a $C_1$ to $C_{20}$ alkyl group, an alkoxy group, an aryl group, a carboxyl group, an aryloxy group, an alkylcarbonyl group, an amide group (—CONH), a nitro group (—NO$_2$), a halogen group, a cyano group (—CN), a silyl group (—SiR$_3$), in which R is selected from hydrogen, an alkyl group and an alkoxy group) and a cyonyl group (—SR, in which R is selected from hydrogen, an alkyl group and an alkoxy group).

More specifically, the bis-phosphite ligand is preferably one or more selected from 2,2'-bis(((2,2'-bisphenoxy)phosphino)-oxy)-3,3',5,5'-tetra-tert-butyl-1,1'-biphenyl (ISO-44), and 2,2'-bis(((2,2'-bisphenoxy)phosphino)-oxy)-3,3'-di-tert-butyl-5,5'-di-methoxy-1,1'-biphenyl).

The polyphosphite ligand is a compound represented by the following Formula 6.

[Formula 6]

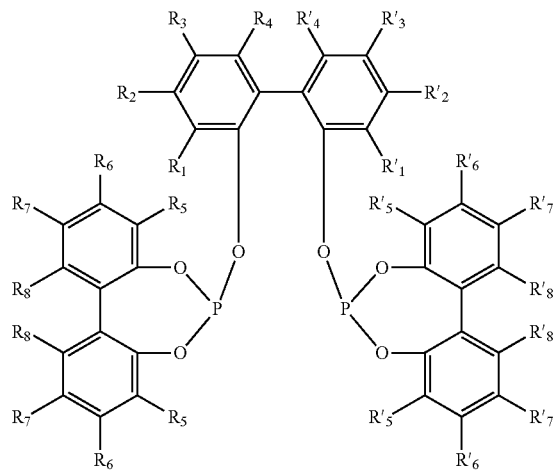

wherein $R_9$ to $R_{12}$, $R_9'$ to $R_{12}'$, $R_9''$ to $R_{12}''$ and $R_9'''$ to $R_{12}'''$ are each independently different or identical, and are selected from hydrogen, a $C_1$ to $C_{20}$ alkyl group, an alkoxy group, an aryl group, a carboxyl group, an aryloxy group, an alkylcarbonyl group, an amide group (—CONH), a nitro group (—NO$_2$), a halogen group, a cyano group (—CN), a silyl group (—SiR$_3$, in which R is selected from hydrogen, an alkyl group and an alkoxy group) and a cyonyl group (—SR, in which R is selected from hydrogen, an alkyl group and an alkoxy group), and n is 1 to 4.

More specifically, the poly-phosphite ligand is at least one selected from 1,4-bis(((4,4'-dimethoxy-6,6'-di-tert-butyl-2,2'-bisphenoxy)phosphino)oxy)phenyl (Ligand B), 4,4'-Bis(((4,4'-dimethoxy-6,6'-di-tert-butyl-2,2'-bisphenoxy)phosphino)oxy)biphenyl (44-BP), and 1,4-bis(((4,4',6,6'-tetra-tert-butyl-2,2'-bisphenoxy)phosphino)oxy)phenyl).

The monophosphite ligand is preferably a compound represented by the following Formula 7.

[Formula 7]

wherein $R_{13}$ to $R_{21}$ and $R_{13}'$ to $R_{16}'$ are each independently different or identical and are selected from hydrogen, a $C_1$ to $C_{20}$ alkyl group, an alkoxy group, an aryl group, a carboxyl group, an aryloxy group, an alkylcarbonyl group, an amide group (—CONH), a nitro group (—NO$_2$), a halogen group, a cyano group (—CN), a silyl group (—SiR$_3$, in which R is selected from hydrogen, an alkyl group and an alkoxy group), and a cyonyl group (—SR, in which R is selected from hydrogen, an alkyl group and an alkoxy group).

More specifically, the mono-phosphite ligand is preferably at least one selected from 4,4'-dimethoxy-6,6'-di-tert-butyl-2,2'-bisphenoxyphosphinoxy-benzene (BPP), 4,4',6,6'-tetra-tert-butyl-2,2'-bisphenoxyphosphinoxy-benzene, 2,2'-bisphenoxyphosphinoxy-2,6-di-tert-butyl-4-methylbenzene, and 2,2'-bisphenoxyphosphinoxy-2,6-di-tertbutyl-benzene.

Each of the contents of bis-phosphite ligand, poly-phosphite ligand and mono-phosphite ligand is preferably 0.5 to 100 moles, more preferably 1 to 20 moles, with respect to one mole of the transition metal catalyst. When the content of the phosphite ligand is lower than 0.5 moles, a problem associated with catalyst stability may occur, and when the content is higher than 100 moles, excess expensive ligand is used without specific benefit, incurring an increase in cost.

The transition metal is preferably a compound represented by the following Formula 8.

$$M(L^1)x(L^2)y(L^3)z \qquad \text{[Formula 8]}$$

wherein M is selected from cobalt (Co), rhodium (Rh) and iridium (Ir), and $L^1$, $L^2$ and $L^3$ are each independently selected from hydrogen, CO, cyclooctadiene, norbornene, chlorine, triphenylphosphine and acetylacetonate, and x, y and z are each independently 0 to 5, under the condition that all of x, y and z are not 0.

The compound represented by Formula 8 is preferably a case in which $L^1$ is CO, $L^2$ is acetylacetonato, and x and y are 2 and 1, respectively, (in a case of acetylacetonate, the compound is a ligand in which each of two oxygen atoms are coordinated to a transition metal, and, in this case, $L^3$ is not present), a case in which $L^1$ is CO, $L^2$ is acetylacetonato, $L^3$ is triphenylphosphine, all of x, y and z are 1, and a case in which $L^1$ is CO, $L^2$ is hydrogen, $L^3$ is triphenylphosphine, and x, y and z are each independently 1, 1 and 3, respectively.

The transition metal catalyst is preferably at least one selected from the group consisting of cobalt carbonyl (Co$(CO)_8$), acetylacetonato dicarbonyl rhodium (Rh(AcAc)$(CO)_2$), acetylacetonato carbonyl triphenylphosphine rhodium (Rh(AcAc)(CO)(TPP)), hydridocarbonyl tri(triphenylphosphine) rhodium (HRh(CO)(TPP)$_3$), acetylacetonato dicarbonyl iridium (Ir(AcAc)(CO)$_2$) and hydridocarbonyl tri(triphenylphosphine) iridium (HIr(CO)(TPP)$_3$), more preferably acetylacetonato dicarbonyl rhodium (Rh(AcAc)(CO)$_2$).

The transition metal catalyst is incorporated in an amount of about 10 to 1000 ppm, as the content of the glass transition metal into a reaction medium of the hydroformylation method, preferably an amount of about 10 to 500 ppm, more preferably an amount of about 25 to 500 ppm, based on the total weight of the reacted products in the reactor. When the content is lower than 10 ppm, it is commercially preferable due to decreased hydroformylation reaction rate, and when the content exceeds 1000 ppm, the transition metal is expensive, causing an increase in cost and more superior effects are not obtained in terms of reaction rate.

In a more specific embodiment, the hydroformylation method includes a) dissolving the bis-phosphite ligand represented by Formula 5 in a solvent to prepare a ligand solution; b) dissolving the poly-phosphite ligand represented by Formula 6 or the mono-phosphite ligand represented by Formula 7 in a solvent to prepare a ligand solution; c) dissolving the transition metal catalyst represented by Formula 8 in a solvent to prepare a catalyst solution; and d) mixing the ligand solutions prepared in steps a) and b), the catalyst solution prepared in step c), and at least one of the compounds represented by Formulae 1 to 4 to prepare a catalyst composition, followed by further reaction with an olefin-based compound and a synthetic gas (comprising carbon monoxide and hydrogen).

Further addition of the olefin-based compound and synthetic gas is preferably carried out when an inner temperature of the reactor reaches a reaction temperature while stirring the catalyst composition, more preferably after an inner temperature of the reactor reaches a reaction temperature and the reaction temperature is stabilized while stirring the catalyst composition. For reference, an inner pressure of the reactor depends on a pressure of reaction gas.

The olefin-based unsaturated compound is preferably a compound represented by the following Formula 9.

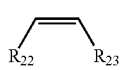

[Formula 9]

wherein $R_{22}$ and $R_{23}$ are each independently selected from hydrogen, a $C_1$ to $C_{20}$ alkyl group, a bromine group (—F), a chlorine group (—Cl), a bromine group (—Br), a trifluoromethyl group (—CF$_3$) and a $C_6$ to $C_{20}$ phenyl group having 0 to 5 substituents (in which subscripts 6 and 20 represent a number of carbon atoms). The substituent of the phenyl group is selected from a nitro group (—NO$_2$), a bromine group (—F), a chlorine group (—Cl), a bromine group (—Br), a methyl group, an ethyl group, a propyl group and a butyl group.

Specifically, the olefin-based unsaturated compound is at least one compound selected from the group consisting of ethene, propene, 1-butene, 1-penthene, 1-hexene, 1-octene, styrene and the like.

The solvent is at least one compound selected from aldehydes including propane aldehyde, butyl aldehyde, valeraldehyde and the like; alcohols including ethanol, pentanol, oxtanol, hexanol and the like; ketones including acetone, methyl ethyl ketone, methyl isobutyl ketone, acetophenone, cyclohexanone and the like; aromatic solvents including benzene, toluene, xylene and the like; halogenated aromatic solvents including orthodichlorobenzene; ethers including tetrahydrofuran, dimethoxyethane, dioxane and the like; halogenated paraffins including methylene chloride; and paraffin hydrocarbon, and is preferably an aldehyde or aromatic solvent.

A mix (volume) ratio of the carbon monoxide to hydrogen (CO:H$_2$) is not particularly limited, is about 5:95 to 70:30, is preferably about 40:60 to 60:40, and is more preferably about 1:1.

A molar ratio of the olefin, carbon monoxide and hydrogen is not particularly limited so long as it is generally used for preparation of aldehyde from olefin.

In the hydroformylation method, the reaction temperature is about 20 to 180° C., preferably about 50 to 150° C., more preferably about 75 to 105° C.

In the hydroformylation method, the reaction pressure is about 1 to 700 bar, preferably 1 to 300 bar.

The reaction in accordance with the hydroformylation method is depicted by the following Reaction Scheme 1 or Reaction Scheme 2.

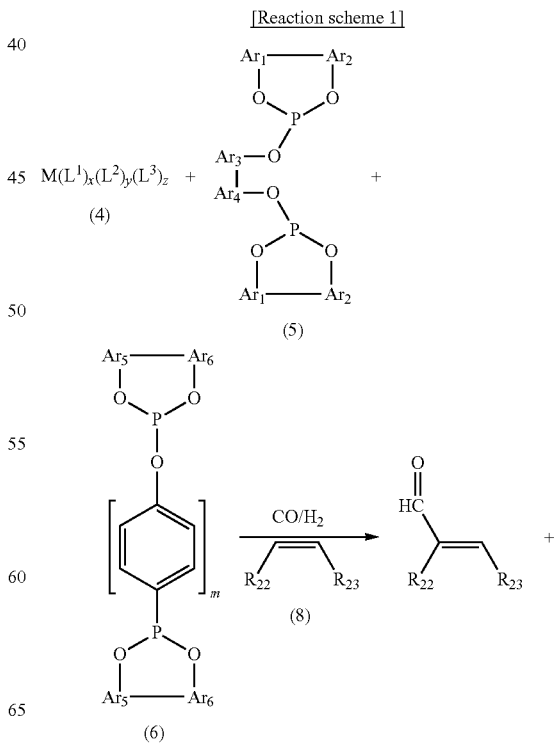

-continued

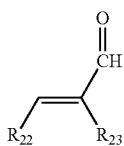

[Reaction scheme 2]

$M(L^1)_x(L^2)_y(L^3)_z$ (4) +

(5) Ar₁—Ar₂, O, P, O, Ar₃—O, Ar₄—O, O, P, O, Ar₁—Ar₂

(7) Ar₇—Ar₈, O, O, P, O, Ar₉

(8) R₂₂, R₂₃

CO/H₂ →

R₂₂, R₂₃, HC=O (on carbon with R₂₂, R₂₃)

+

R₂₂, R₂₃ with CH=O

Now, the present invention will be described in more detail with reference to the following examples. These examples are only provided to illustrate the present invention and should not be construed as limiting the scope and spirit of the present invention.

EXAMPLES

Example 1

0.0125 g (0.049 mmol) of acetylacetonato dicarbonyl rhodium (Rh(AcAc)(CO)₂) as a catalyst, 0.092 g (0.49 mmol) of 3-(benzylidene)pentane-2,4-dione (BPD) as a compound represented by Formula 1, 0.204 g (0.24 mmol) of 2,2'-bis (((2,2'-bisphenoxy)phosphino)-oxy)-3,3',5,5'-tetra-tert-butyl-1,1'-biphenyl (ISO-44) as a bis-phosphite ligand, and 0.215 g (0.24 mmol) of 1,4-bis(((4,4'-dimethoxy-6,6'-di-tert-butyl-2,2'-bisphenoxy)phosphino)oxy)phenyl (Ligand B) as a poly-phosphite ligand were dissolved in butylaldehyde as a solvent to obtain 50 g of a solution. This solution was put into a 200 ml autoclave reactor.

A reactive gas comprising propene (olefin), CO and H2 at a molar ratio of 1:1:1 was put into the reactor, an inner pressure of the reactor was adjusted to 6 bar and then maintained and, at the same time, reaction was performed while stirring at 80° C. for one hour.

Example 2

A process was performed in the same manner as in Example 1, except that 0.114 g (0.488 mmol) of 2-benzylidene-1H-indene-1,3(2H)-dione (BID) as the compound of Formula 2 was used instead of the compound represented by Formula 1.

Example 3

A process was performed in the same manner as in Example 1, except that 0.72 g (0.482 mmol) of benzeneacetic acid, R-imino-(BAAI) as the compound of Formula 3 was used instead of the compound represented by Formula 1.

Example 4

A process was performed in the same manner as in Example 1, except that 0.132 g (0.488 mmol) of (Z)-2-phenylmethylene-3(2H)-benzo[b]thiophen-3-one-1,1-dioxide (BMBTD) as the compound of Formula 4 was used instead of the compound represented by Formula 1.

Comparative Examples 1 to 2

A process was performed in the same manner as in Example 1, except that the compound represented by Formula 1 was not incorporated (Comparative Example 1), or 0.09 g (0.49 mmol) of 1,2-epoxydodecane (EDD) was used instead of the compound represented by Formula 1 (Comparative Example 2).

Test Example

N/I selectivity and catalyst activity of aldehydes prepared in Examples 1 to 4 and Comparative Examples 1 and 2 were measured in accordance with the following method. The results thus obtained are shown in Table 1 below.

N/I selectivity: value obtained by dividing an amount of produced normal-butylaldehyde by an amount of produced iso-butylaldehyde and the amount of produced aldehyde was determined by gas chromatography (GC) analysis.

Catalyst activity (kgmol(BAL)/mol(Rh)/h): value obtained by dividing the total amount of aldehyde produced during the reaction by a molecular weight of butylaldehyde, concentration of used catalyst, and reaction time.

Aging test: catalyst activity was measured at different aging times while a gas having a molar ratio of CO:H2 of 1:1 was incorporated into the solution, while maintaining an inner pressure of the reactor at 10 bar and stirring at 120° C.

TABLE 1

| | Stabilized compound | Fresh catalyst activity(kgmol (BAL)/mol(Rh)/h) | N/I selectivity | Aging time | | |
|---|---|---|---|---|---|---|
| | | | | Fresh | 2.5 hr | 5.0 hr |
| Comp. Ex. 1 | — | 2.23 | 20.0 | 2.23 | 1.87 | 1.25 |
| Comp. Ex. 2 | EDD | 2.20 | 19.5 | 2.20 | 1.95 | 1.32 |
| Ex. 1 | BPD | 2.15 | 20.5 | 2.15 | 2.01 | 1.51 |
| Ex. 2 | BDI | 2.21 | 20.1 | 2.21 | 2.05 | 1.57 |
| Ex. 3 | BAAI | 2.05 | 21.9 | 2.05 | 1.85 | 1.35 |
| Ex. 4 | EMBTD | 2.25 | 20.8 | 2.25 | 2.09 | 1.60 |

As can be seen from Table 1 above, the hydroformylation methods in which compounds 1 to 3 according to the present invention are incorporated (Example 1 to 3) exhibit high N/I selectivity and stably maintain catalyst activity, as compared to cases in which the compounds 1 to 3 are not incorporated (Comparative Example 1) or a case in which an epoxide compound is incorporated (Comparative Example 2).

As apparent from the fore-going, the present invention advantageously provides a hydroformylation method in which a specific α, β-unsaturated carbonyl compound is incorporated during a hydroformylation reaction to prevent alkyl phosphite decomposed from a phosphite ligand from acting as a catalyst poison, thereby improving reaction yield and inhibiting decomposition of ligand and catalyst.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A hydroformylation method for preparing aldehyde by reacting an olefin-based unsaturated compound with carbon monoxide and hydrogen in the presence of a transition metal-phosphite complex catalyst produced from a transition metal catalyst and a phosphite ligand, wherein the reaction is carried out by further incorporating one or more of compounds represented by the following Formulae 1 to 4:

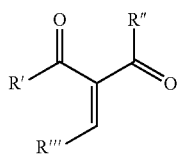

[Formula 1]

(wherein R' and R" each independently represent a substituted or unsubstituted alkyl group having 1 to 3 carbon atoms, and R'" represents a substituted or unsubstituted aryl group having 6 to 12 carbon atoms),

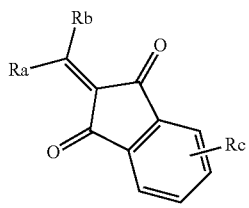

[Formula 2]

(wherein Ra represents hydrogen, Rb represents a substituted or unsubstituted aryl group having 6 to 12 carbon atoms, and Rc represents hydrogen or an alkyl group)

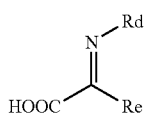

[Formula 3]

(wherein Rd and Re each independently represent a substituted or unsubstituted aryl group having 6 to 12 carbon atoms)

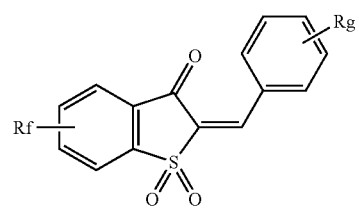

[Formula 4]

(wherein Rf and Rg each independently represent hydrogen or an alkyl group).

2. The method according to claim 1, wherein the transition metal is a compound represented by the following Formula 8:

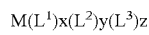

$M(L^1)x(L^2)y(L^3)z$ [Formula 8]

(wherein M is selected from cobalt (Co), rhodium (Rh) and iridium (Ir), and $L^1$, $L^2$ and $L^3$ are each independently selected from hydrogen, CO, cyclooctadiene, norbornene, chlorine, triphenylphosphine and acetylacetonato, and x, y and z are each independently 0 to 5, under the condition that all of x, y and z are not 0).

3. The method according to claim 2, wherein the transition metal catalyst is at least one selected from the group consisting of cobalt carbonyl (Co(CO)₈), acetylacetonato dicarbonyl rhodium (Rh(AcAc)(CO)₂), acetylacetonato carbonyl triphenyl phosphine rhodium (Rh(AcAc)(CO)(TPP)), hydridocarbonyl tri(triphenylphosphine) rhodium (HRh(CO)(TPP)₃), acetylacetonato dicarbonyl iridium (Ir(AcAc)(CO)₂) and hydridocarbonyl tri(triphenylphosphine) iridium (HIr(CO)(TPP)₃).

4. The method according to claim 1, wherein the phosphite ligand is a mixture of a bisphosphite ligand and a polyphosphite ligand, or a mixture of a bisphosphite ligand and a monophosphite ligand.

5. The method according to claim 4, wherein the bisphosphite ligand is represented by the following Formula 5:

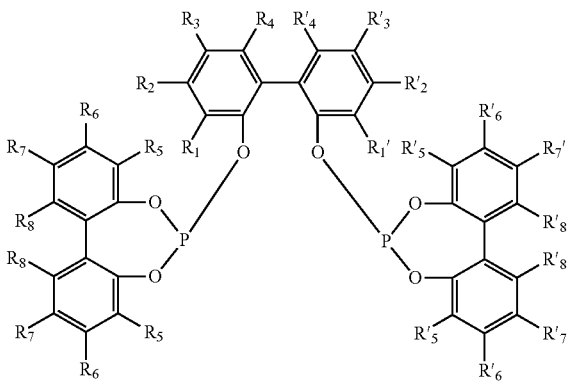

[Formula 5]

wherein $R_1$ to $R_8$ and $R_1'$ to $R_8'$ are each independently different or identical, and represent hydrogen, a $C_1$ to $C_{20}$ alkyl group, an alkoxy group, an aryl group, a carboxyl group, an aryloxy group, an alkylcarbonyl group, an amide group (—CONH), a nitro group (—NO₂), a halogen group, a cyano group (—CN), a silyl group (—SiR₃, in which R is selected from hydrogen, an alkyl group and an alkoxy group) and a cyonyl group (—SR, in which R is selected from hydrogen, an alkyl group and an alkoxy group).

6. The method according to claim 4, wherein the polyphosphite ligand is a compound represented by the following Formula 6:

[Formula 6]

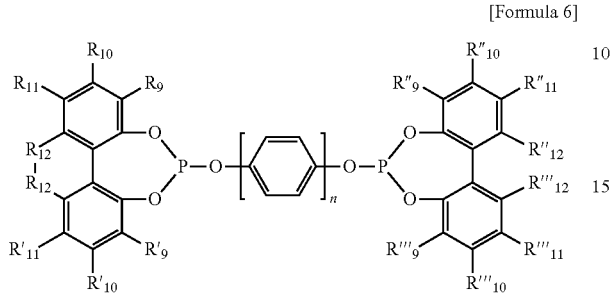

wherein $R_9$ to $R_{12}$, $R_9'$ to $R_{12}'$, $R_9''$ to $R_{12}''$ and $R_9'''$ to $R_{12}'''$ are each independently different or identical, and are selected from hydrogen, a $C_1$ to $C_{20}$ alkyl group, an alkoxy group, an aryl group, a carboxyl group, an aryloxy group, an alkylcarbonyl group, an amide group (—CONH), a nitro group (—NO$_2$), a halogen group, a cyano group (—CN), a silyl group (—SiR$_3$, in which R is selected from hydrogen, an alkyl group and an alkoxy group) and a cyonyl group (—SR, in which R is selected from hydrogen, an alkyl group and an alkoxy group), and n is 1 to 4, and the monophosphite ligand is a compound represented by the following Formula 7

[Formula 7]

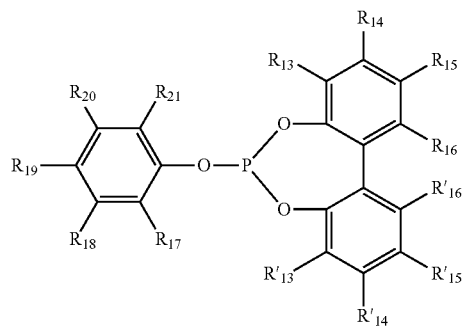

wherein $R_{13}$ to $R_{21}$ and $R_{13}'$ to $R_{16}'$ are each independently different or identical and are selected from hydrogen, a $C_1$ to $C_{20}$ alkyl group, an alkoxy group, an aryl group, a carboxyl group, an aryloxy group, an alkylcarbonyl group, an amide group (—CONH), a nitro group (—NO$_2$), a halogen group, a cyano group (—CN), a silyl group (—SiR$_3$, in which R is selected from hydrogen, an alkyl group and an alkoxy group), and a cyonyl group (—SR, in which R is selected from hydrogen, an alkyl group and an alkoxy group).

7. The method according to claim 1, wherein the transition metal catalyst is present in an amount of 25 to 500 ppm, as the content of the glass transition metal in a reaction medium, based on the total weight of the reacted products in the reactor.

8. The method according to claim 1, wherein the phosphite ligand is present in an amount of 1 to 100 moles, with respect to one mole of the transition metal catalyst.

9. The method according to claim 1, wherein the compounds represented by Formulae 1 to 4 are incorporated in an amount of 0.5 to 10 moles, based on one mole of the phosphite ligand.

* * * * *